United States Patent
Sung

(10) Patent No.: US 8,469,028 B2
(45) Date of Patent: Jun. 25, 2013

(54) RESPIRATOR ASSEMBLY

(75) Inventor: Ching-Lung Sung, Taichung County (TW)

(73) Assignee: SLS Medical Technology Co., Ltd., Taichung (TW)

( * ) Notice: Subject to any disclaimer, the term of this patent is extended or adjusted under 35 U.S.C. 154(b) by 636 days.

(21) Appl. No.: 12/662,787

(22) Filed: May 4, 2010

(65) Prior Publication Data

US 2010/0282260 A1 Nov. 11, 2010

(30) Foreign Application Priority Data

May 5, 2009 (TW) ................................ 98114919 A

(51) Int. Cl.
- *A62B 7/10* (2006.01)
- *A62B 7/00* (2006.01)
- *A62B 19/00* (2006.01)
- *A62B 23/02* (2006.01)
- *A61M 16/00* (2006.01)

(52) U.S. Cl.
USPC ............ 128/205.12; 128/204.18; 128/205.27; 128/205.29

(58) Field of Classification Search
USPC ............ 128/200.24, 201.25, 203.12, 204.16, 128/204.18, 205.12, 205.27–205.29; 55/467; 96/63

See application file for complete search history.

(56) References Cited

U.S. PATENT DOCUMENTS

| | | | |
|---|---|---|---|
| 4,430,995 A * | 2/1984 | Hilton ...................... | 128/204.21 |
| 6,666,209 B2 * | 12/2003 | Bennett et al. ............ | 128/200.24 |
| 2006/0048782 A1 * | 3/2006 | Gossweiler ............... | 128/205.12 |
| 2010/0078027 A1 * | 4/2010 | Ogasahara ................ | 128/205.12 |
| 2010/0139657 A1 * | 6/2010 | Chalvignac et al. ...... | 128/204.22 |

* cited by examiner

*Primary Examiner* — Justine Yu
*Assistant Examiner* — Valerie L Skorupa
(74) *Attorney, Agent, or Firm* — Bacon & Thomas, PLLC

(57) ABSTRACT

A respirator assembly is composed of a respirator, an air purifier, and a connection tube. The respirator includes a first housing having an inflow unit and an air intake. A first pumping unit is located in the first housing for sucking the air through the inflow unit and exhausting the air through the air outtake. The air purifier includes a second housing having an air intake and an outflow unit. A second pumping unit is located in the second housing for sucking the air through the air intake and exhausting the air through the outflow unit. The outflow unit includes a natural-air outlet and a respirator outlet. The connection tube includes two ends, one of which is connected with the respirator outlet and the other is connected with the inflow unit. Accordingly, the respirator assembly can reduce the frequency of replacing the respiratory screen and enhance the quality of filtering the air.

6 Claims, 4 Drawing Sheets

RESPIRATOR ASSEMBLY

BACKGROUND OF THE INVENTION

1. Field of the Invention

The present invention relates generally to a respirator, and more particularly, to a respirator assembly.

2. Description of the Related Art

A conventional respirator can suck the air by a high-speed fan located therein to provide the air for the patient of respiratory disease. Because most of the indoor air contains suspended particles, like dust, pollen, bacteria, and virus, the conventional respirator filters the suspended particles by a cotton-based screen. How many the suspended particles can be filtered depend on the capacity and material of the screen. Although the screen having smaller meshes can filter smaller particles, the density of the screen is higher to increase the resistance to the air, such that of the patient of low-pressure treatment breathing level may have breathing difficulty. Besides, such screen is disposable to have a short service life to increase the cost in operating the respirator.

There are reusable cotton-based screen. Although such reusable cotton-based screen can be detached for washing, its meshes are larger and subject to structural damage incurred in the process of the washing to allow smaller suspended particles or bacteria to pass therethrough. Besides, most of the conventional respirators each can be additionally connected with a filter mounted to its air outtake to prevent the suspended particles from passing through the screen and prevent the patient's lung from further injury caused by those suspended particles or bacteria. However, the additional filter in connection with the respirator used for the long-term residential treatment increases the medical cost for the patient.

SUMMARY OF THE INVENTION

The primary objective of the present invention is to provide a respirator assembly, which can provide a patient with high-quality air for breathing to prevent the patient's lung from further injury.

The secondary objective of the present invention is to provide a respirator assembly, which can decrease the frequency of replacing its screen to lower the total cost.

The foregoing objectives of the present invention are attained by the respirator assembly composed of a respirator, an air purifier, and a connection tube. The respirator includes a first housing having an inflow unit and an air intake. A first pumping unit is located in the first housing for sucking the air through the inflow unit and exhausting the air through the air outtake. The air purifier includes a second housing having an air intake and an outflow unit. A second pumping unit is located in the second housing for sucking the air through the air intake and exhausting the air through the outflow unit. The outflow unit includes a natural-air outlet and a respirator outlet. The connection tube includes two ends, one of which is connected with the respirator outlet and the other is connected with the-inflow unit.

DETAILED DESCRIPTION OF PREFERRED EMBODIMENTS

Figure 1:
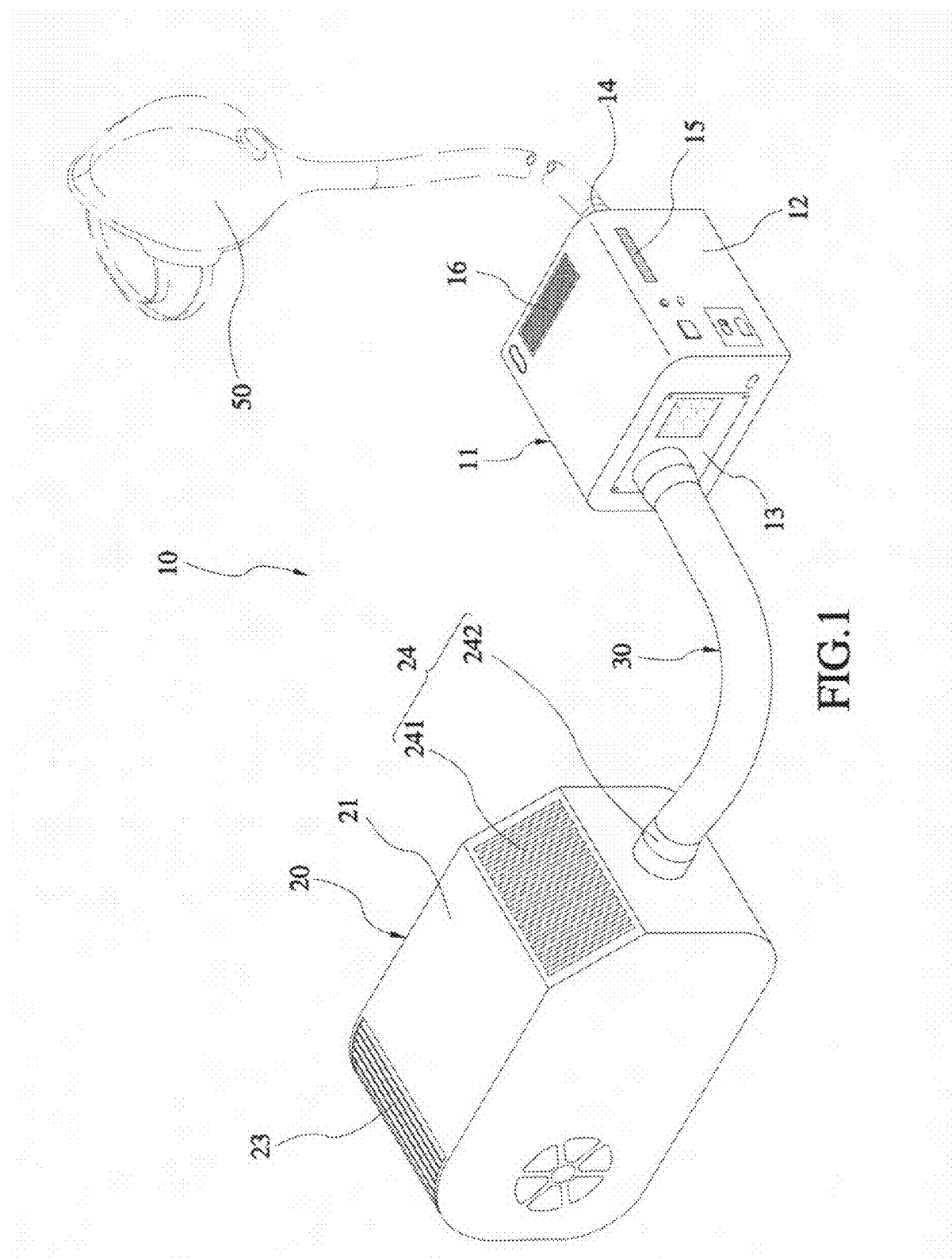
FIG. 1 is a perspective view of a preferred embodiment of the present invention.
Figure 2:
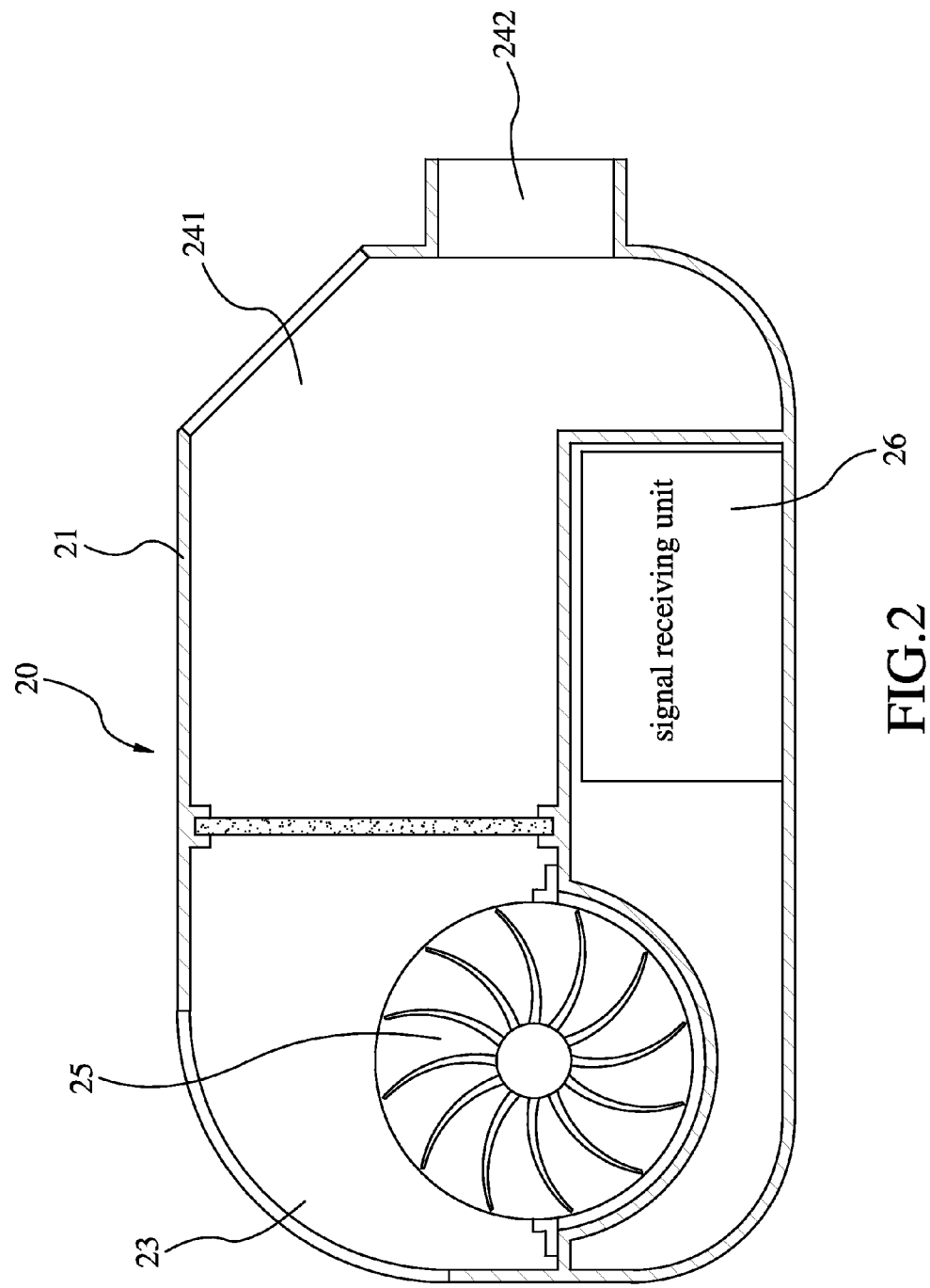
FIG. 2 is a sectional view of the preferred embodiment of the present invention, showing the air purifier.
Figure 3:
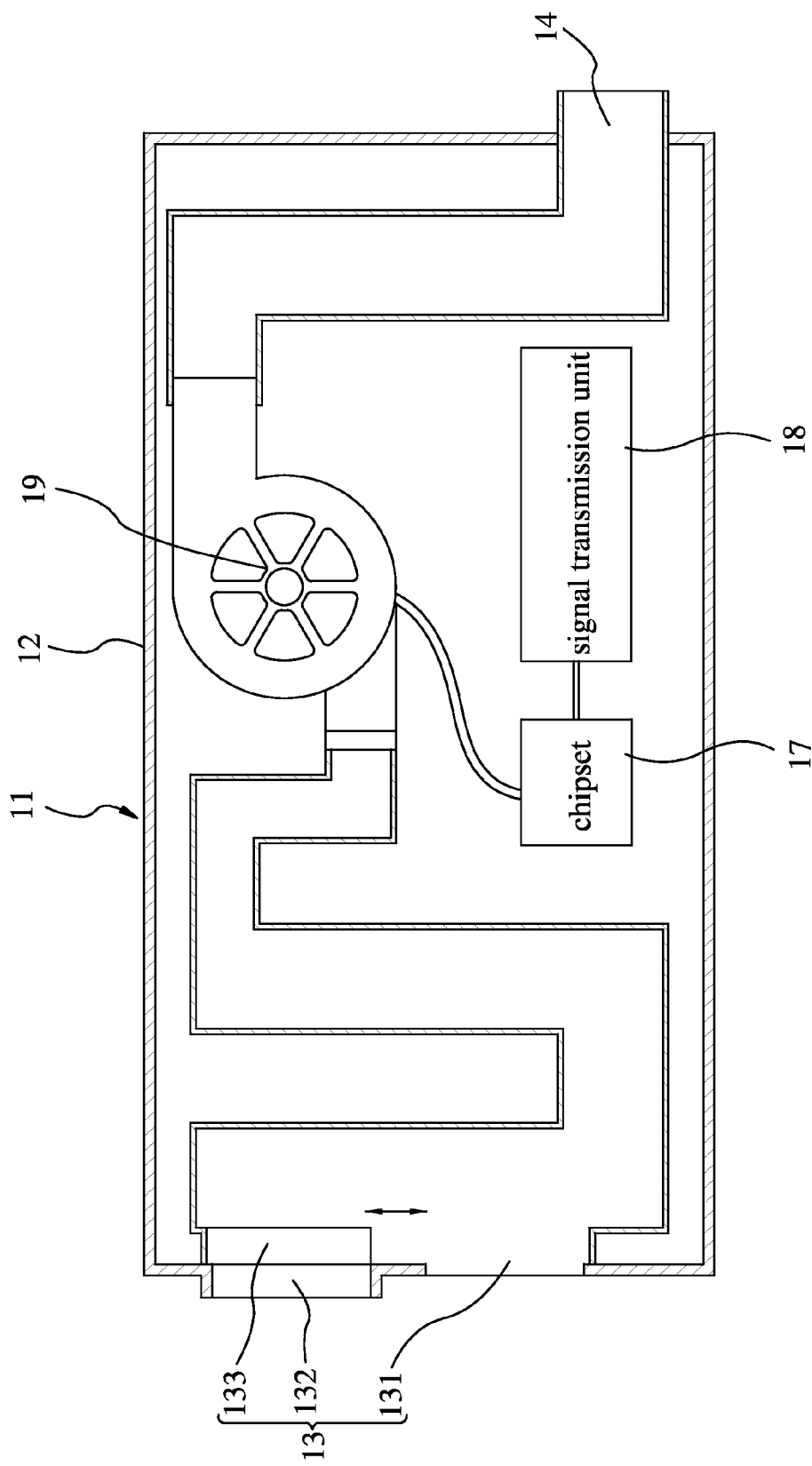
FIG. 3 is another sectional view of the preferred embodiment of the present invention, showing the respirator.
Figure 4:
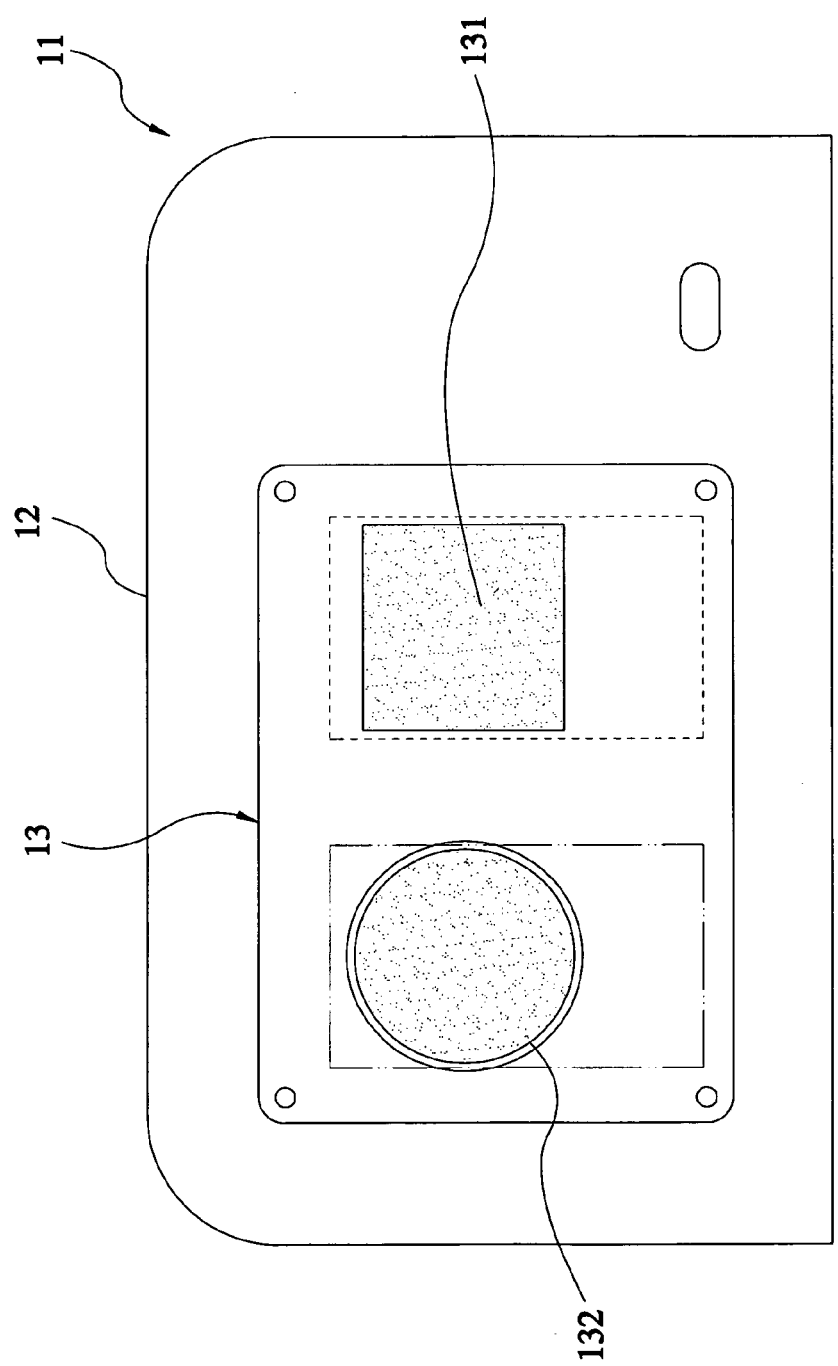
FIG. 4 is another schematic view of the preferred embodiment of the present invention, showing the inflow unit of the respirator.

Referring to FIGS. 1-4, a respirator assembly 10 constructed according to a preferred embodiment of the present invention is composed of a respirator 11, an air purifier 20, and a connection tube 30. The detailed descriptions and operations of these elements as well as their interrelations are recited in the respective paragraphs as follows.

The respirator 11 includes a first housing 12 having an inflow unit 13 and air outtake 14. The inflow unit 13 has a natural-air inlet 131, an air-purifier inlet 132, and a control valve 133. In this embodiment, the control valve 133 is an electro-magnetic valve. The control valve 133 can manually or electrically open or close the natural-air inlet 131 and the air-purifier inlet 132. When the control valve 133 opens the natural-air inlet 131, the control valve 133 closes the air-purifier inlet 132. When the control valve 133 closes the natural-air inlet 131, the control valve 133 opens the air-purifier inlet 132. A microparticle detector 16 and a suspended-particle concentration display device 15 are mounted outside the first housing 12. The microparticle detector 16 is to detect the concentration of the suspended particles in the air outside the first housing 12. A chipset 17, a signal transmission unit 18, and a first pumping unit 19 are mounted inside the first housing 12. In this embodiment, the first pumping unit 19 is an induction fan. The first pumping unit 19 can suck the air through the natural-air inlet 131 or the air-purifier inlet 132 and then exhaust the air through the air outtake 14. The chipset 17 is electrically connected with the suspended-particle concentration display device 15 and the microparticle detector 16. The microparticle detector 16 can detect suspended particles, convert such detection into a signal, and then transfer the signal to the chipset 17 in such a way that the chipset 17 can digitalize the concentration of the suspended particles and enables the suspended-particle concentration display device 15 to display the digitalized result. The chipset 17 is electrically connected with the first pumping unit 19 to allow adjustment of the rotary speed of the first pumping unit 19 in such a way that every outflow of the air exhausting through the air outtake 14, no matter whether any inflow of the air entering the respirator 11 comes from the natural-air inlet 131 or the air-purifier inlet 132, is constant after the adjustment of the rotary speed of the pumping unit 19. The chipset 17 can drive the control valve 133 to open or close the natural-air inlet 131 and the air-purifier inlet 132. The chipset 17 is electrically connected with the signal transmission unit 18 to allow the signal transmission unit 18 to be controlled by the chipset 17 for transmitting a signal to the air purifier 20.

The air purifier 20 includes a second housing 21 having an air intake 23 and an outflow unit 24, both of which run therethrough. A second pumping unit 25 and a signal receiving unit 26 are mounted inside the second housing 21. The second pumping unit 25 can suck the air through the air intake 23 and then exhaust the air through the outflow unit 24. The outflow unit 24 is provided with a natural-air outlet 241 and a respirator outlet 242. The signal receiving unit 26 can receive the signal of the signal transmission unit 18 to activate the air purifier 20.

The connection tube 30 includes two ends, one of which is connected with the respirator outlet 242 and the other is connected with the air-purifier inlet 132.

Referring to FIG. 1 again, in light of the above structure, while the user intends to operate the respirator assembly 10, the user can connect one end of the connection tube 30 to the respirator outlet 242 and the other end thereof to the air-purifier inlet 132 and then connect a respiratory mask 50 to the air outtake 14; next, the user can electrically drive the control valve 133 to open the natural-air inlet 131 and close the air-purifier inlet 132 and then activate the respirator 11 to allow the first pumping unit 19 to suck the air through the natural-air inlet 131 and exhaust the air through the air outtake 14 to the respiratory mask 50. The user can also manually drive the control valve 133 to open the air-purifier inlet 132 to activate the air purifier 20, thus allowing that the inflow of the respirator 11 comes from the air purifier 20.

When the inflow of the respirator 11 comes from the natural-air inlet 131 and the digitalized result of the concentration of the suspended particles rises up to a predetermined value, the chipset 17 can control the control valve to open the air-purifier inlet 132 and enable the signal transmission unit 18 to transmit a signal to the air purifier 20 to activate the air purifier 20 and then the air purifier 20 can suck the air through the natural-air inlet 23; next, the air passes through the second pumping unit 25 to exhaust through the outflow unit 24, specifically through the natural-air outlet 241 to an ambient environment for purifying the air therearound and through the respiratory outlet 241 and the connection tube 30 into the respirator 11; meanwhile, the chipset 17 can also adjust the rotary speed of the first pumping unit 19, while the air purifier 20 is activated, to make the outflow of the air from the air outtake 14 be constant.

In conclusion, the present invention can enhance the efficiency of filtering the suspended particles in the air and heighten the air quality to reduce the frequency of replacing the screen of the respirator to further lower the cost for the respirator, thus preventing the user's lung from further injury.

Although the present invention has been described with respect to a specific preferred embodiment thereof, it is in no way limited to the specifics of the illustrated structures but changes and modifications may be made within the scope of the appended claims.

What is claimed is:

1. A respirator assembly comprising:
a respirator having a first housing having an air outtake, a first pumping unit and an inflow unit being located in the first housing, the inflow unit having a natural-air inlet and an air-purifier inlet, the first pumping unit being provided for sucking the air through the inflow unit and exhausting the air through the air outtake;
an air purifier having a second housing having an air intake, an outflow unit and a second pumping unit being located in the second housing, the second pumping unit being provided for sucking the air through the air intake and exhausting the air through the outflow unit, the outflow unit having a natural-air outlet and a respirator outlet; and
a connection tube having two ends, one of which is connected with the respirator outlet and the other is connected with the air-purifier inlet.

2. The respirator assembly as defined in claim 1, wherein the inflow unit further comprises a control valve for opening or closing the natural-air inlet and the air-purifier inlet; while opening the natural-air inlet, the control valve closes the air-purifier inlet; while closing the natural-air inlet, the control valve opens the air-purifier inlet.

3. The respirator assembly as defined in claim 2 further comprising a chipset, wherein the chipset is mounted in the first housing.

4. The respirator assembly as defined in claim 3 further comprising a microparticle detector for detecting the concentration of suspended particles in the air outside the first housing.

5. The respirator assembly as defined in claim 4 further comprising a suspended-particle concentration display device, wherein the suspended-particle concentration display device is mounted outside the first housing; the chipset can digitalize the detected concentration of the suspended particles and the suspended-particle concentration display device can display a result of the digitalized concentration of the suspended particles.

6. The respirator assembly as defined in claim 5, wherein the respirator further comprises a signal transmission unit; the air purifier further comprises a signal receiving unit; while the result reaches a threshold, the signal transmission unit transmits a signal to the signal receiving device to activate the air purifier.

* * * * *